United States Patent
Wey

(10) Patent No.: US 10,610,699 B2
(45) Date of Patent: Apr. 7, 2020

(54) THERAPEUTIC DEVICE USING FAR-INFRARED RADIATION

(71) Applicant: Albert Chin-Tang Wey, Westmont, IL (US)

(72) Inventor: Albert Chin-Tang Wey, Westmont, IL (US)

(73) Assignee: Aldi Far-IR Products, Incorporated, Westmont, IL (US)

( * ) Notice: Subject to any disclaimer, the term of this patent is extended or adjusted under 35 U.S.C. 154(b) by 267 days.

(21) Appl. No.: 15/651,729

(22) Filed: Jul. 17, 2017

(65) Prior Publication Data

US 2017/0312539 A1 Nov. 2, 2017

Related U.S. Application Data

(63) Continuation-in-part of application No. 13/870,773, filed on Apr. 25, 2013, now abandoned.

(51) Int. Cl.
*A61N 5/06* (2006.01)

(52) U.S. Cl.
CPC ............ *A61N 5/0613* (2013.01); *A61N 5/06* (2013.01); *A61N 2005/066* (2013.01); *A61N 2005/0645* (2013.01); *A61N 2005/0656* (2013.01); *A61N 2005/0659* (2013.01)

(58) Field of Classification Search
CPC ....... A61N 5/06; A61N 5/0656; A61N 5/0659
USPC .............................................. 607/88–93, 100
See application file for complete search history.

(56) References Cited

U.S. PATENT DOCUMENTS

| | | | |
|---|---|---|---|
| 4,976,706 A | 12/1990 | Aki | |
| 5,138,133 A | 8/1992 | Sakurada | |
| 6,108,581 A | 8/2000 | Jung | |
| 6,363,285 B1 | 3/2002 | Wey | |
| 6,516,229 B1 | 2/2003 | Wey | |
| 6,531,341 B1 | 3/2003 | Peterson | |
| 6,591,142 B1 | 7/2003 | Dea | |
| 7,617,815 B2 | 11/2009 | Wey | |
| 8,285,391 B2 | 10/2012 | Malak | |
| 8,366,757 B2 | 2/2013 | Oliveira | |
| 2005/0177191 A1 | 8/2005 | Saitou | |
| 2006/0226378 A1 | 10/2006 | Yabiku | |
| 2007/0198070 A1 | 8/2007 | Oliveira | |
| 2009/0193797 A1* | 8/2009 | Wey | F01N 3/2066 60/300 |
| 2011/0186010 A1 | 8/2011 | Wey | |
| 2012/0061232 A1 | 3/2012 | Wey | |
| 2012/0089208 A1 | 4/2012 | York | |

\* cited by examiner

*Primary Examiner* — Nathan J Jenness
(74) *Attorney, Agent, or Firm* — IpHorgan Ltd.

(57) ABSTRACT

This invention relates to a therapeutic device for treating a human or animal body, comprising an array of infrared-emitting elements in an attachment means for attaching to the body part to be treated, said infrared-emitting elements being in the form of sintered ceramic plates and made from a mixture of infrared-emitting oxides having specific spectral luminance covering at least a part of the 3-7 micrometer wavelength spectrum and having a peak wavelength between 3 and 7 micrometers, that provides an effective means to healing the body. A locally administrable heating means may be used for escalated healing effects.

16 Claims, 1 Drawing Sheet

THERAPEUTIC DEVICE USING FAR-INFRARED RADIATION

CROSS-REFERENCE TO RELATED APPLICATION

This application is a continuation-in-part of application Ser. No. 13/870,773, filed Apr. 25, 2013, which is herein incorporated by reference in its entirety.

BACKGROUND

Field of Invention

This invention relates to a therapeutic device for treating a human or animal body, comprising an array of infrared-emitting elements in an attachment means that follows the contour of the body part to be treated, said infrared-emitting element being an infrared-emitting ceramic plate made of a mixture of infrared-emitting oxides having specific spectral luminance covering at least a part of 3-7 um (micrometer) wavelength spectrum and having a peak wavelength between 3 and 7 um. More specifically, the invention relates to a therapeutic device having a spectral luminance covering at least a part of 3-6 um wavelength spectrum and having a peak wavelength at approximately 4 um, that provides an effective means to healing the body. A locally administrable heating means may be used for escalated healing effects.

Description of Prior Art

According to Organic Chemistry photoexciting molecules of water and organic compounds with infrared (IR) photons shorter than 20 um (micrometer) in wavelength can increase their vibrational energy, in forms of stretching and/or bending vibrations. Such effects have been described in textbooks. The photoexcited molecules tend to loosen up their intramolecular bonding, resulting in forming smaller-size clusters with increased mobility and circulation in human and animal bodies.

Several types of therapeutic devices have been developed over the years for improving the health of a human body using far infrared (FIR) radiation, including the present inventor's previous patents (U.S. Pat. Nos. 6,363,285, 6,516,229 and 7,617,815) and others (e.g. U.S. Pat. Nos. 6,591,142, 8,285,391, and 8,366,757), each of which are herein incorporated by reference in their entireties. These devices might have demonstrated success to some degree in the purposed applications, but only with limited effects.

"Far infrared radiation" is not a scientific term, but is commonly understood to refer to electromagnetic radiation in 3-20 um wavelength range. The term is used to indicate the category of the infrared spectrum to which certain IR-emitting devices belong, but the use of the term does not necessarily imply the use of the entire 3-20 um wavelength range. In practice, a narrower wavelength band is typically used because any methods and materials must follow known science.

Every molecule has its own infrared absorption bands based on the types and force constants of covalent bonds in the molecular structure. The molecule may absorb well-defined wavelengths of infrared radiation to create one of six types of bond vibrations: symmetrical stretching, anti-symmetrical stretching, scissoring, rocking, wagging, and twisting. Each type of vibration responds to the absorption of a certain wavelength in 3-20 um range. Any infrared radiation outside the absorption bands will be transferred merely as heat that causes only local rotation or translation of the entire molecule. As such, it is critical that the ceramic composite only emits infrared radiation covering the desirable wavelengths.

The present inventor has engaged in far-infrared radiation research for decades, specifically in the 3-20 um wavelength range. IR absorptions in said wavelength range have been scientifically identified, called "infrared signature," in Organic Chemistry, and the present inventor is the first scientist to make the connection between theory and utilization, hoping to bring the technology to life for benefitting the society. Continuous research has bettered the present inventor's knowledge of FIR radiation and its effects on matter at a molecular level. The gained knowledge has led the present inventor to developing enhanced IR-emitting ceramic composites in the desired 3-20 um wavelength band, which have been disclosed in U.S. Pat. No. 7,617,815 and U.S. patent application Ser. No. 12/657,961 for other applications by the present inventor.

While researching and making IR-emitting ceramic composites, the present inventor has come to realizing several facts regarding the properties and better use of the newly developed IR-emitting ceramic composites, which are disclosed herein as follows.

It is well known that the IR emission rate is proportional to the total surface area (A) of an IR-emitter comprising IR-emitting ceramic composite; the larger the total surface is, the more radiation the IR-emitter may supply. However, the first fact that the present inventor has learned is that, in addition, the emission strength is also proportional to the photon generation rate of the IR-emitter, which is closely related to the total mass (M) of the IR-emitting ceramic composite. In order to have the highest possible emission strength, the IR-emitter, must be designed to have an optimal total-mass to total-surface-area ration (M/A).

Furthermore, it is known that infrared radiation results from thermal vibrations of dipole moments associated with a specific crystal structure. Dipole moments, in turn, are created by asymmetry in the crystal system. Each particle in infrared-emitting ceramic powder essentially has a dipole moment that may radiate infrared at selective wavelengths, depending on its composition and crystal structure. The infrared radiation from the products of prior art is a collective work of unaligned dipole moments from individual ceramic powders, which has a relatively low radiation strength due to coherence of radiation. In contrast, a controlled-sintering process that follows hard-pressing of the mixture of ceramic powders, as employed in the present application, helps bring grains together. It increases the compaction ratio of the crystal system, with increased density, reduced surface area, and decreased free energy of the system.

In addition, sintering increases the contact area between grains by removing pores and thus enhances ion diffusion and dispersion at the grain boundary. Ions such as $Al^{3+}$, $Ca^{2+}$, $K^+$, $Fe^{2+}$, $Mg^{2+}$, $O^{2-}$, $H^+$, and so on, can freely relocate in the crystal system for re-crystallization and directional grain growth. As a result, controlled-sintering at a temperature above 1100° C. may help align individual dipole moments to result in coherent dipole moments of the system and significantly increase infrared radiation a hundredfold, compared to agglomerated particles that are bonded with resin, as used in the prior art. Consequently, a well-engineered IR-emitting ceramic plate would outperform a mere aggregate of IR-emitting oxide powders or particles that are disposed in forms of pads, sheets, or foams, as disclosed in the prior art.

The second fact that the present inventor has learned is that it would be difficult to design a broadband IR-emitter that could have uniformly distributed its radiation energy over the entire 3-20 um wavelength range. In theory, the majority of available radiation energy from an IR-emitter is often associated with shorter wavelengths (i.e. higher frequencies), governed by the energy formula for electromagnetic (EM) waves: E=hv, where h is Planck constant, and v frequency. Moreover, the peak wavelength where the maximum flux density per unit wavelength interval emerging from an IR-emitter will displace toward shorter wavelengths as the temperature of the emitter increases, known as Wien's Displacement Law. This inevitably results in radiation energy being over-strengthened in short wavelengths and meantime weakened in long wavelengths, which may leave some groups of water molecules and/or chemical compounds in human or animal body unexcited or less-excited.

To overcome this problem, the present inventor has disclosed in his previous patent (U.S. Pat. No. 7,615,815) that the desirable IR-emitters with specific peak wavelength and spectral luminance profile in 3-20 um wavelength range can be respectively made with selected oxides. In practice, the use of various IR-emitters in different wavelength bands will enhance the overall IR activation effect on molecules in body fluids and thus magnify the healing effects.

The third fact the present inventor has learned is that adding an effective amount of pyroelectric material into the mixture of IR-emitting metal oxides would significantly increase the resultant emissions at the desired 3-20 um wavelengths.

By definition, pyroelectricity is the ability of certain materials to generate temporary voltage when they are heated or cooled. The change in temperature slightly modifies the positions of the atoms in the crystal structure, such that the polarization of the material changes. This polarization change gives rise to a voltage across the crystal. If the temperature stays constant at its new value, the pyroelectric voltage will gradually disappear due to leakage current. A large ceramic plate would be less susceptible to temperature change than a smaller plate. Consequently, it is better to use an array of small IR-emitting ceramic plates for utilizing the pyroelectricity of the material than to simply use a large plate having the same volume and mass as the total of all small plates. Furthermore, a locally administrable heating device may be used to control the temperature of each IR-emitting ceramic plate for manipulating the pyroelectricity of the plates, which would dramatically increase the healing effects of the present invention on the targeted body part.

Based on aforementioned findings, the present inventor has discovered a new approach using an array of IR-emitting ceramic plates in an attachment means for enhanced IR healing effects on a human or animal body, which differs from all therapeutic devices disclosed in prior art that have been implemented in forms of powders, pads, sheets, beads, or a single large plate.

Objects and Advantages

Accordingly, one object of this invention is to provide a therapeutic device with amplified infrared emission in the desirable 3-20 um wavelength range;

Another object of this invention is to provide a therapeutic device having a specific spectral luminance in the 3-7 um wavelength range and having a peak wavelength between 3 and 7 um;

Another object of this invention is to provide a therapeutic device having an array of infrared elements comprising at least two different types of ceramic plates having different specific spectral luminance overlapping at least a part of the 3-7 um wavelength range and having different peak wavelengths between 3 and 7 um.

Another object of the present invention is to provide a therapeutic device for effectively increasing the IR healing effects on human or animal body;

Also, another object of the present invention is to provide a simple, easy-to-use, and maintenance-free therapeutic device that is flexible to attach to any part of human or animal body that requires treatment.

These objectives are achieved by a therapeutic device comprising an array of IR-emitting elements. Said IR-emitting element is an IR-emitting ceramic plate made of essentially a mixture of selected IR-emitting metal oxides having specific spectral luminance covering at least a part of 3-20 um wavelength spectrum. Said array of IR-emitting elements can be secured in a flexible attachment means and placed at close proximity of the body part that requires treatment.

Other objects, features, and advantages of the present invention will hereinafter become apparent to those skilled in the art from the following description.

SUMMARY OF THE INVENTION

In accordance with the present invention a therapeutic device comprises an array of IR-emitting elements in an attachment means that follows the contour of the body part to be treated, said IR-emitting element being an IR-emitting ceramic plate made of a mixture of IR-emitting oxides having specific spectral luminance covering at least a part of 3-20 um (micrometer) wavelength spectrum, providing an effective means to healing human or animal body. A locally administrable heating means may be used to provide localized heating for escalated healing effects.

Figure 1:
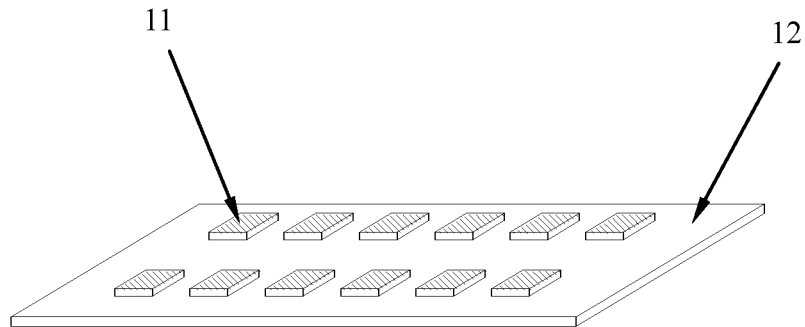
FIG. 1 shows a perspective view of one embodiment of the present invention with an array of two (rows) by six (columns) IR-emitting ceramic plates disposed on a substrate.

| Reference Numerals in Drawings: | |
|---|---|
| 11 Infrared-emitting ceramic plate | 12 Attachment means |
| 21 Heating element | 22 Encasement means |
| 31 Covering means | |

DETAILED DESCRIPTION OF THE INVENTION

The IR-emitting ceramic plates of the present invention can be fabricated by the following process. First, prepare a mixture of powders of IR-emitting metal oxides, such as disclosed in U.S. Pat. Nos. 6,363,285, 6,516,229, and 7,617,815 by the present inventor, in theoretical percentages by weight for intended peak wavelengths and spectral luminance. An effective amount of pyroelectric material may be added to the mixture for amplified IR emissions. The pyroelectric material, tourmaline in the present invention, may be any of 5-40% by weight. Lastly, the mixture of metal oxides and pyroelectric material, along with bonding agents, catalysts, and stabilizers, is press-molded to the desired shapes and sintered in a furnace at a temperature of 1100 deg. C. or above. Several samples were prepared accordingly for concept-demonstrating experiments of the present invention.

FIG. 1 shows a perspective view of an embodiment of the present invention, in which twelve IR-emitting ceramic plates 11 are mounted on a substrate 12, in a formation of two (rows) by six (columns), or a 2×6 array, which may be easily wrapped around the body part that requires treatment. In other deployments, IR-emitting ceramic plates may be secured simply by wires or strings to keep the formation. The ceramics of the present invention can take any sizes, shapes, forms, styles, patterns, and in any thickness, though a rectangular or circular plate is preferred for the ease of fabrication. Depending on the applications, the plates may have dimensions as small as in a 2-mm-diameter circle (or a 2 mm by 3 mm rectangle) up to a 50-mm-dia. circle (or 40 mm by 50 mm rectangle), with a thickness from 1 mm up to 10 mm.

Figure 2:
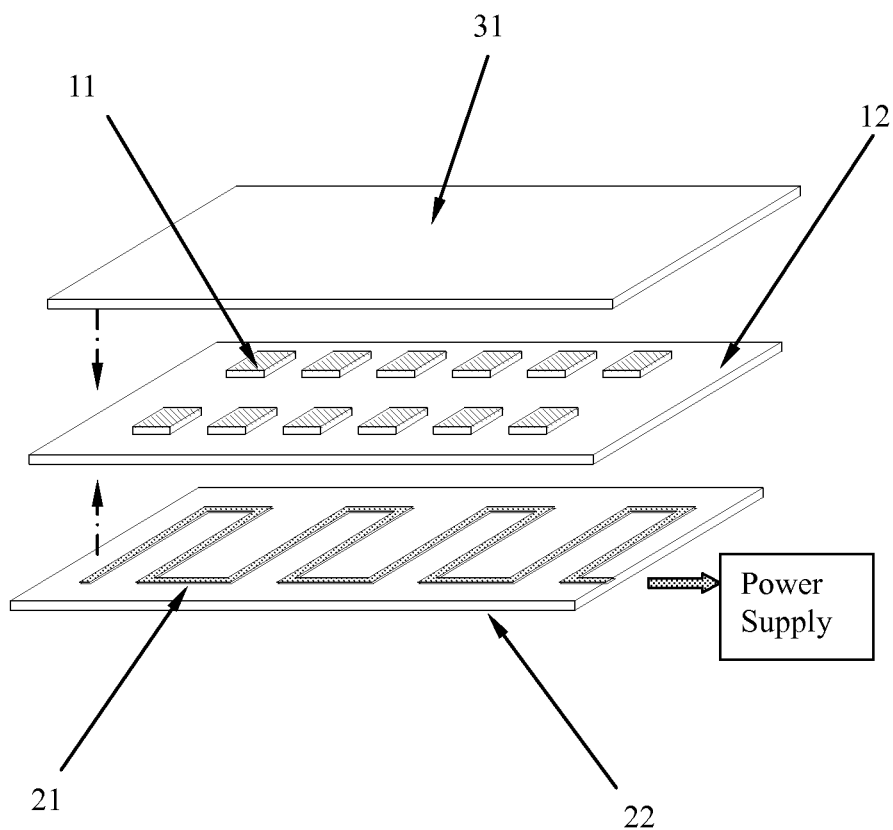
FIG. 2 shows a perspective view of another embodiment of the present invention with an array of two-by-six IR-emitting ceramic plates sandwiched by a covering sheet and a heating means in an encasement.

FIG. 2 shows a perspective view of another embodiment of the present invention that the 2×6 array of IR-emitting ceramic plates 11 shown in FIG. 1 are sandwiched by a covering sheet 31 and a heating element 21 in an encasement 22.

The IR-emitting ceramic plates 11 absorb ambient radiation heat and convert the heat into IR photons. IR radiation from the IR-emitter 11 will last indefinitely, wherever the ambient temperature is greater than Absolute Zero, 0 deg. K or −273 deg. C. Evidently, body heat is a natural heat source for the IR-emitters. Yet, an external heat source may be used in the case that both intensified IR emission and shorter IR wavelengths are required for accelerated healing. As described before, the peak wavelengths and spectral luminance of the IR-emitters 11 will displace toward shorter wavelengths as their temperatures increase.

The dominating content of body fluids is body water. Approximately 60-65% of body water is contained within the cells (in intracellular fluid) with the other 35-40% of body water contained outside the cells (in extracellular fluid). This fluid component outside of the cells includes the fluid between the cells (interstitial fluid), lymph and blood. It is worth noting that water can absorb infrareds at wavelengths around 2.87, 3.05, 3.65 and 6.08 um, which all place at the lower end of the IR-emitter's 3-20 um wavelengths spectrum. The use of a heating device will drive IR energy toward shorter wavelengths, ideal for accelerated healing that requires a strong absorption of IR emissions by body water.

The specific spectral luminance profile and peak wavelengths emitted by an IR-emitting ceramic composite are influenced not only by the composition, but also by the processing parameters involved, such as the temperature and duration of heating and cooling cycles and particle size. In order to simplify the fabrication of new IR-emitting ceramics, the present inventor has developed a base mixture of materials that provides a standardized platform for easy modification. Rather than choosing individual materials and processing parameters for each new ceramic, one merely alters the weight percentages of key elements in the composite system. In particular, the percentages of ferric oxide, chromic oxide, cobalt oxide, and minority oxides may be altered.

Several ceramic plate samples were designed and made for concept demonstration. The base mixture of IR-emitting oxides contain, by weight, 20% silicate, 20% alumina, 24% zirconia, 4% sodium monoxide, 3% potassium oxide, 3% ferric oxide, 5% chromic oxide, 4% cobalt oxide, 2% all other minority oxides, and 15% tourmaline. While the base ingredients provide for far infrared emissions generally, the key elements that collectively control peak wavelength and spectral luminance are: ferric oxide, chromic oxide, cobalt oxide, and nickel oxide. For example, increasing the weight percentage (wt. %) of CoO or NiO helps enhance emissions at lower wavelengths in the 3-6 um range. Replacing the CoO with $Fe_2O_3$ and $Cr_2O_3$ may move the peak wavelength and spectral luminance to longer wavelengths in the 8-16 um range. Thus, various samples with distinctive wt. % of the aforementioned ingredients in the base mixture were made for tailored peak wavelength and specific spectral luminance profile, specifically emphasizing on 3-7 um wavelength range for a better IR activation effect on body fluids.

Three sample compositions were made by varying the wt. % of oxides in the base mixture. Each of the samples contains 20% silicate, 20% alumina, 24% zirconia, 4% sodium monoxide, 3% potassium oxide, and 2% minority oxides. However, Sample-1 comprises less ferric oxide and less chromic oxide than the base compound, with the difference made up by adding nickel oxide. Sample-2 comprises the base compound. Sample-3 comprises more ferric oxide than the base compound with no cobalt oxide. The results are displayed in Table 1 below.

TABLE 1

Peak Wavelength and Spectral Luminance of Sample Ceramic Compositions

| Sample | Sample-1 | Sample-2 | Sample-3 |
| --- | --- | --- | --- |
| Peak Wavelength (um) | 4 | 8 | 13 |
| Spectral Luminance (um) | 3-6 | 7-11 | 11-16 |
| Wt. % $Fe_2O_3$ | 2 | 3 | 7 |
| Wt. % $Cr_2O_3$ | 2 | 5 | 5 |
| Wt. % CoO | 4 | 4 | 0 |
| Wt. % NiO | 4 | 0 | 0 |

It should be appreciated from the results in Table 1 that the spectral luminance profile may be significantly shifted by modifying the weight percentages of a few oxides in the base composition. It should also be appreciated that Sample 1 would be particularly effective for therapeutic treatment of a human or animal body because its spectral luminance profile (range of 3-6 um and peak wavelength at 4 um) corresponds to the IR absorption of water at 2.87, 3.05, 3.65, and 6.08 um.

Of course, additional samples may be created with wt. % that vary from Samples 1-3 disclosed above. For example, a ceramic containing wt. % between Sample-1 and Sample-2 (e.g. 2.5 wt. % $Fe_2O_3$, 3.5 wt. % $Cr_2O_3$, 4 wt. % CoO, and 2 wt. % NiO) can be expected to have a peak wavelength between 4 and 8 um and a spectral luminance overlapping both the 3-6 um range and the 7-11 um range. Those additional compositions are considered to be within the scope of the invention.

The therapeutic device according to the present invention may contain IR-emitters in different wavelength bands to enhance the overall IR activation effect on molecules in body fluids and thus magnify the healing effects. In particular, the array may contain plates having different individual compositions. For example, an array of 12 plates may contain a first set of 6 plates according to Sample-1 and second set of 6 plates with a composition between Sample-1 and Sample-2. The result of such a combination would be a broader overall wavelength band, with distinct peak wavelengths in the 3-7 um spectrum. It should be appreciated that more than two types of plates may be used, and the plates may be distributed in different patterns and different relative quantities in the array to achieve the overall desired effect.

Two sizes of ceramic plates were made: "Sample-A" (3 mm long, 3 mm wide, and 1 mm thick) and "Sample-B" (30 mm long, 20 mm wide, and 5 mm thick). "Sample-A" ceramic plates were used for the treatment of gum inflammation, tooth pain, and pyorrhea alveolaris, while "Sample-B" ceramic plates were used for the treatment of sprains, strains, muscular spasm, phantom limb sensation, peripheral vascular diseases, and rheumatoid arthritis. In some of the cases a heating device was required. Encouraging results have been observed.

CONCLUSION, RAMIFICATIONS, AND SCOPE

According to the present invention, a therapeutic device comprises an array of IR-emitting elements in an attachment means, said IR-emitting element being an IR-emitting ceramic plate made of a mixture of IR-emitting oxides having specific spectral luminance covering at least a part of 3-20 (micrometer) um wavelength spectrum, for providing an effective means to healing human or animal body.

The invention has been described above. Obviously, numerous modifications and variations of the present invention are possible in light of the above teachings. Such variations are not to be regarded as a departure from the spirit and scope of the invention and all such modifications as would be obvious to one skilled in the art are intended to be included within the scope of the following claims.

I claim:

1. A therapeutic device comprising: an array of infrared-emitting elements secured in a flexible means for attaching the array to a body part to be treated, the array comprising at least first and second infrared-emitting elements, the first infrared-emitting element being a first ceramic plate comprising a first mixture of infrared-emitting oxides, the first ceramic plate having a first specific spectral luminance covering at least a part of the 3-7 micrometer wavelength spectrum and having a first peak wavelength between 3 and 7 micrometers, the second infrared-emitting element being a second ceramic plate comprising a second mixture of infrared-emitting oxides, the second ceramic plate having a second specific spectral luminance covering at least a part of the 3-7 micrometer wavelength spectrum and having a second peak wavelength between 3 and 7 micrometers, the second specific spectral luminance being different from the first specific spectral luminance and the second peak wavelength being different from the first peak wavelength, wherein each of the first and second ceramic plates have at least a 4 square millimeter surface area for emitting infrared radiation toward the body, and wherein each of the first and second ceramic plates has been sintered by heating to a temperature between 1100° C. and 1300° C.

2. The device according to claim 1, wherein the first and second mixtures of infrared-emitting oxides each comprise silicate, alumina, zirconia, sodium monoxide, potassium oxide, ferric oxide, chromic oxide, and cobalt oxide.

3. The device according to claim 2, wherein the first and second mixtures of infrared-emitting oxides each comprise 20 wt. % silicate, 20 wt. % alumina, 24 wt. % zirconia, 4 wt. % sodium monoxide, 3 wt. % potassium oxide, and 2% other minority oxides.

4. The device according to claim 3, wherein the second mixture of infrared-emitting oxides comprises a higher wt. % of ferric oxide and a lower wt. % of chromic oxide than the first mixture of infrared-emitting oxides.

5. The device according to claim 3, wherein the first and second mixture of infrared-emitting oxides further comprise nickel oxide, and wherein the first mixture of infrared-emitting oxides comprises a higher wt. % of nickel oxide than the second mixture of infrared-emitting oxides.

6. The therapeutic device according to claim 1, wherein the first and second mixtures of infrared emitting oxides each comprise at least one of: silicate, alumina, zirconia, sodium monoxide, potassium oxide, ferric oxide, chromic oxide, cobalt oxide, magnesium oxide, lithium oxide, calcium oxide, and titanium oxide.

7. The therapeutic device according to claim 1, wherein 5-40 wt. % in each of the first and second mixtures of infrared-emitting oxides is pyroelectric material comprising tourmaline.

8. The therapeutic device according to claim 1, wherein the array of first and second infrared-emitting elements comprises at least 12 total ceramic plates arranged in 2 rows and 6 columns.

9. The therapeutic device according to claim 1, wherein the flexible means comprises a flexible substrate and wherein the array of infrared-emitting elements is mounted on the flexible substrate.

10. The therapeutic device according to claim 9, further comprising a covering sheet, a heating element, and an encasement, wherein the array, the flexible substrate, and the heating element are disposed between the covering sheet and the encasement.

11. The device according to claim 1, wherein each of the first and second ceramic plates is shaped as a cylinder having a diameter of 2-50 mm and a thickness of 1-10 mm.

12. The device according to claim 1, wherein each of the first and second ceramic plates is rectangular in shape and has a width of 2-40 mm, a length of 3-50 mm, and a thickness of 1-10 mm.

13. The device according to claim 1 wherein each of the first and second ceramic plates is 3 mm wide, 3 mm long, and 1 mm thick.

14. The device according to claim 1, wherein each of the first and second ceramic plates is 20 mm wide, 30 mm long, and 5 mm thick.

15. A method for treatment of a human or animal body part, comprising: a) providing an array of first and second infrared-emitting elements secured in a flexible means for attaching the array to a body part to be treated, he first infrared-emitting element being a first ceramic plate comprising a first mixture of infrared-emitting oxides, the first ceramic plate having a first specific spectral luminance covering at least a part of the 3-7 micrometer wavelength spectrum and having a first peak wavelength between 3 and 7 micrometers, the second infrared-emitting element being a second ceramic plate comprising a second mixture of infrared-emitting oxides, the second ceramic plate having a second specific spectral luminance covering at least a part of the 3-7 micrometer wavelength spectrum and having a second peak wavelength between 3 and 7 micrometers, the second specific spectral luminance being different from the first specific spectral luminance and the second peak wavelength being different from the first peak wavelength and each of the first and second ceramic plates having at least a 4 square millimeter surface area for emitting infrared radiation toward the body, wherein each of the first and second ceramic plates has been sintered by heating to a temperature between 1100° C. and 1300° C.; b) attaching the array of infrared-emitting elements to the body part; and c) irradiating the body part with infrared radiation emitting by the infrared-emitting elements.

16. The method according to claim 15, further comprising heating the infrared-emitting elements with a heating element to achieve escalated healing effects.

* * * * *